Figure 1:
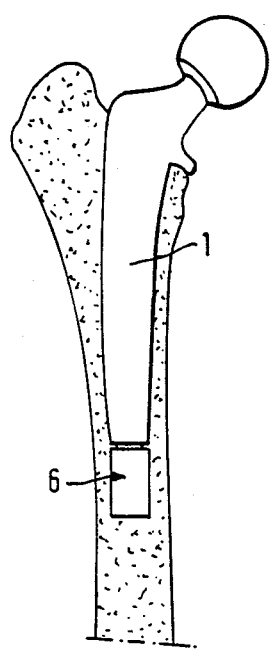

United States Patent [19]

Hoffman et al.

[11] Patent Number: 4,921,499
[45] Date of Patent: May 1, 1990

[54] ADJUSTABLE PROSTHESIS

[75] Inventors: Erik L. Hoffman, HL Roosendaal; Antonius L. J. Hopstaken, PW Roosendaal en Nispen, both of Netherlands

[73] Assignee: Ordev B.V., Netherlands

[21] Appl. No.: 253,730

[22] Filed: Oct. 5, 1988

[30] Foreign Application Priority Data

Oct. 5, 1987 [NL] Netherlands ............... 8702371

[51] Int. Cl.⁵ .............................................. A61F 2/28
[52] U.S. Cl. ....................................... 623/16; 623/23; 606/60; 606/78
[58] Field of Search ............... 623/16, 18, 19, 20, 623/22, 23

[56] References Cited

U.S. PATENT DOCUMENTS

| | | | |
|---|---|---|---|
| 4,011,602 | 3/1977 | Rybicki et al. | 3/1.9 |
| 4,728,333 | 3/1988 | Masse et al. | 623/23 |
| 4,756,711 | 7/1988 | Mai et al. | 623/16 |

FOREIGN PATENT DOCUMENTS

| | | |
|---|---|---|
| 2306782 | 11/1976 | European Pat. Off. . |
| 0145166 | 6/1985 | European Pat. Off. . |
| 0187903 | 7/1986 | European Pat. Off. ............ 623/23 |
| 0201442 | 12/1986 | European Pat. Off. . |
| 0229578 | 7/1987 | European Pat. Off. . |
| 1548964 | 7/1979 | United Kingdom . |

*Primary Examiner*—David J. Isabella
*Attorney, Agent, or Firm*—Peter L. Michaelson

[57] ABSTRACT

A fixation element for securing a prosthesis in a bone, whereby the effective diameter of the fixation element can be increased by increasing the temperature of at least one element of a material which shrinks or expands when heated, such as shape memory metal, by means of an inductive magnetic field, whereby the change in shape generated with the shrinkage or expansion of the material is converted into an increase in diameter of the fixation element.

6 Claims, 1 Drawing Sheet

ADJUSTABLE PROSTHESIS

This invention relates to a prosthesis, and in particular to a fixation element for the fixation of the prosthesis to a bone.

It is known for a prosthesis for example, a joint prosthesis, to be secured to a long bone by inserting a pin-shaped part of the prosthesis into the longitudinal cavity in the long bone, which has been made to fit, and in which it is fixed by means of a press fit. There are cementless and cemented prostheses. One problem encountered here is that, after some time, play arises between the pin of the prosthesis and the cavity of the bone as a result of changes, including natural changes, which occur in the bone; in particular owing to the change in ratio between endostal and periostal bone production. Naturally, in both cementless and cemented prostheses, mechanical factors partly determine the duration of correct fitting and fixation to the bone.

It is an object of the present invention to remove the above play by non-operative means.

According to the invention, a prosthesis is provided with one or more fixation elements whose effective diameter can be increased by increasing the temperature of at least one element of a material which shrinks or expands when heated, such as shape memory metal, by means of a strong inductive magnetic field, whereby the change in shape generated with the shrinkage or expansion of the material is converted into an increase in diameter of the fixation element.

In a preferred embodiment of the invention, the fixation element comprises a tapered core adapted to be secured to a prosthesis, and a substantially cylindrical sleeve arranged to surround said core, said sleeve being composed of segments which on the side facing the tapered core are of complementary-tapered configuration, the core and the sleeve segments being interconnected by rods of shape memory metal extending between the core and each of the segments.

When an increase in diameter of the fixation element is desired, it is only necessary to heat the rods of shape memory metal to above its transition temperature in question by means of an inductive magnetic field, as a result of which the rods undergo a shortening or extension and thereby displace the sleeve segments over the tapered core towards the wider part of the core, thereby increasing the effective sleeve diameter and re-fixing the prosthesis firmly with the bone.

In a further elaboration of the invention, slots are formed in the core and/or in the sleeve segments, said slots forming, in pairs, chambers each adapted to receive a shape memory metal rod, the bottom of the slots in the core and the shape memory rods being formed with complementary transverse ridges which, in cooperation with spring means urging the segments against the core, fix the segments axially relatively to the core.

It is observed that, as described in European patent application No. 0145166, the use of shape memory metal for medical uses, such as heart valves, catheters and canulas, contraceptive aids, connecting plates for use with bone fractures, orthodontic means, bone nails, and also fixation elements to be placed in a bone cavity, is known per se. As far as shape memory metal is used in bone connections, however, the change in shape of the metal in passing a temperature limit is used to effect some sort of clamping connection. By itself, this already has the disadvantage that a prosthesis or connecting element, at body temperature, continues to exert a pressure on the bone, and may cause pressure necrosis. The subject of the present invention, namely, using the properties of shape memory metal to correct a prosthesis which has been functioning for some time by non-operative means is not known from the literature.

Figure 2:
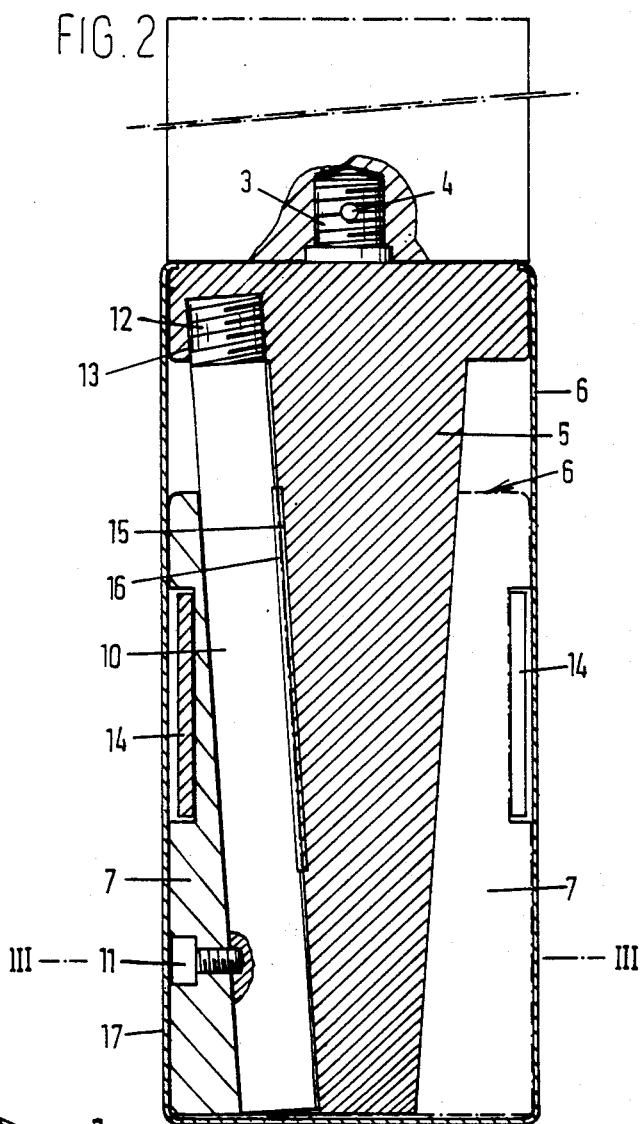
Figure 3:
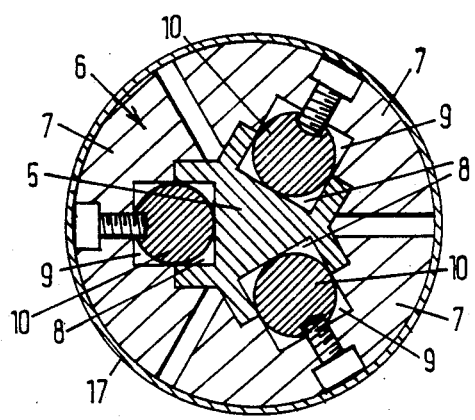

One embodiment of the prosthesis fixation element according to the present invention will now be described, by way of example, with reference to the accompanying drawings, in which FIG. 1 diagrammatically shows a thighbone (femur) with a hip joint prosthesis therein;

FIG. 2 is a longitudinal sectional view, partly in side-elevation, of a fixation element; and FIG. 3 is a bottom view of the fixation element of FIG. 2, at the level of fixation pin 11, in cross-section on the line A—A.

Referring to the drawings, the bottom end of a hip prosthesis 1 is provided with a tapered core 5, secured to it by means of a threaded pin 3 with a lock screw 4 or by means of a Morse-Taper connection, around which a sleeve 6 is provided which, in the embodiment shown, is composed of three segments 7, the inside of which is of complementary tapered configuration relative to core 5. Formed in the core are three axial slots 8, and in each of the segments 7, an axial slot 9 is formed. Slots 8 and 9 form, pairwise, a chamber for receiving a rod 10 of shape memory metal.

As shown in FIG. 2, each rod 10 is connected by means of a socket screw 11 or a rod of shape memory metal shrinking at about 60° C., to a sleeve segment 7, while at the opposite end of the shape memory metal rod 10 the latter is received by means of a screw connection 12 in a hole 13 in core 5. The sleeve segments are further kept clamped on to core 5 by a spring 14.

In the embodiment shown, the bottom of the slots 8 in the core are formed with cross-notches 15, and the rods 10 have complementary notches 16.

The prosthesis fixation element according to the invention functions as follows.

Before the prosthesis is placed in the bone, the shape memory metal rods 10 are stretched. With a titanium-nickel alloy, which has the property of undergoing a change in length at a given temperature range of, for example, about 8%, the rods are stretched by 8% of their basic length. This means that, when heated to above the transition temperature of about 43° C., they undergo 8% shrinkage.

The prosthesis with the fixation element according to the invention is now press-fitted in the bone.

If, after some time, it turns out that, owing to recession of the bone tissue, play establishes itself, i.e., the hole around the fixation element has become too wide, the temperature in rods 10 is increased to about 43° C. by means of a strong inductive magnetic field, as a result of which these undergo a shrinkage of, maximally, 8%. As a result of this shrinkage, the sleeve segments 7 are pulled upwards, as viewed in FIG. 2, to the wider part of core 5, as a result of which the effective sleeve diameter is increased until the play in the bone cavity is removed. The prosthesis is now re-fixed without operative surgery being needed.

The shrinkage of rods 10, in spite of the interengagement of the teeth 15 and 16, in the slot bottoms in the core and in the rod surfaces facing these, is possible by virtue of the fact that at the extremely strong shrinkage forces occurring during the shrinkage of shape memory metal, the rods can recede relatively to the core against the force of spring 14. When the "end position" is reached (i.e., the diameter required) the teeth 15 and 16 are re-locked, and the axial position of sleeve segments 7 relative to core 5 is again fixed. It is noted that, in principle, it is immaterial whether, in the prosthesis fixation element according to the invention, the rods 10 are of expanding or shrinking shape memory metal, if the correct place of fixation in the core 5 is selected. It is further noted that, when the links are shifted, in the first instance the prosthesis, which also has a tapered form, is pulled downwards. As a result, the entire prosthesis is better fixed. Subsequently, the sleeve diameter is increased.

If desired, the prosthesis can be removed when the screws 11 have been removed surgically. When a rod of shape memory metal is used for the connection 11, which shrinks when the temperature is increased, the fixation between rod 10 and link 7 can be removed by increasing the temperature of the rod to about 60° C.

It is clear that, depending on the ultimate use, various embodiments of the core and the links can be selected. Depending on the available space in the bone, a fitting fixation element can be secured to a prosthesis. Prior to installation in the bone, the whole can be enveloped by a flexible sheath 17 of, for example, silicone rubber.

We claim:

1. A fixation element for securing a prosthesis in a bone, said element comprising:
   a tapered core adapted to be secured to a prosthesis;
   a substantially cylindrical sleeve configured to surround said core, said sleeve defining a plurality of discrete segments, each of said segments having an inner surface complementary tapered to engage the tapered core;
   a plurality of shape memory metal rods each having a transition temperature and being capable of changing shape in response to a change in temperature above or below the transition temperature; and
   said rods extending between and interconnecting the core and each of the segments, whereby a change in shade of the rods is converter into an increase in diameter of the fixation element so as to effect a secure fixation of the prosthesis in the bone.

2. A fixation element as claimed in claim 1 further comprising slots formed in said core and/or in said sleeve segments, said slots forming, in pairs, chambers each adapted to receive a shape memory metal rod, the bottom of the slots in the core and the shape memory rods being formed with complementary transverse ridges which, in cooperation with spring means urging the segments against the core, fix the segments axially relative to the core.

3. A fixation element for securing a prosthesis in a bone, said element comprising:
   a first element having a first wedge shaped surface;
   a second element configured to surround said first element and having an inner second surface with a complementary wedge shape to engage said first surface;
   at least one shape memory rod having a transition temperature and being capable of changing shape in response to a change in temperature above or below the transition temperature; and
   said rod being arranged with respect to said first and second elements such that the change in the shape of the rod is converted into relative motion between said first and second elements so as to produce an increase in diameter of the fixation element thereby effecting a secure fixation in the bone of the fixation element and a prosthesis connected thereto.

4. The fixation element in claim 3 wherein said second element is a substantially cylindrical sleeve defining at least one segment having the inner second surface and said first element is a core situated within said sleeve and aligned for axial movement relative to said core and along a common axis thereof, and wherein the diameter of the sleeve changes in response to relative axial movement between said sleeve and said core produced by the change in the shape of the rod so as to cause the sleeve to abuttingly engage against said bone and provide said secure fixation of the prosthesis.

5. The fixation element in claim 3 wherein said rod extends between and interconnects the first and second elements.

6. The fixation element in claim 5 wherein said second element is a substantially cylindrical sleeve defining at least one segment having the inner second surface and said first element is a core situated within said sleeve and aligned for axial movement relative to said core and along a common axis thereof, and wherein the diameter of the sleeve changes in response to relative axial movement between said sleeve and said core produced by the change in the shape of the rod so as to cause the sleeve to abuttingly engage against said bone and provide said secure fixation of the prosthesis.

* * * * *